United States Patent [19]

Salisbury

[11] 4,053,280
[45] Oct. 11, 1977

[54] INSTRUMENT TRAY AND SOAK BASIN COMBINATION

[75] Inventor: Thomas E. Salisbury, Highland Park, Ill.

[73] Assignee: American Hospital Supply Corporation, Evanston, Ill.

[21] Appl. No.: 679,570

[22] Filed: Apr. 23, 1976

[51] Int. Cl.² .................... A61L 3/00; B08B 3/04; B65D 81/00
[52] U.S. Cl. .................... 21/87; 21/90; 21/105; 134/25 A; 134/135; 206/363
[58] Field of Search ........... 21/87, 99, 86, 90, 100, 21/105, 91; 220/90.4; 206/518, 363; 134/25 A, 135

[56] References Cited

U.S. PATENT DOCUMENTS

| | | | |
|---|---|---|---|
| 1,187,364 | 6/1916 | Monnot | 21/87 |
| 1,239,834 | 9/1917 | Smith | 134/135 |
| 1,850,524 | 3/1932 | Whittaker | 21/87 |
| 3,250,283 | 5/1966 | Reinfeld | 21/87 X |
| 3,437,423 | 4/1969 | Mondiadis | 21/105 X |
| 3,697,223 | 10/1972 | Kovalcik et al. | 21/105 X |
| 3,807,954 | 4/1974 | McDonald | 21/87 |
| 3,966,408 | 6/1976 | Drennen et al. | 21/87 |

Primary Examiner—Barry S. Richman
Attorney, Agent, or Firm—Tilton, Fallon, Lungmus, Chestnut & Hill

[57] ABSTRACT

An instrument tray and basin for use in soaking, rinsing, and draining urological instruments and other instruments prior to use, and for supporting such instruments during transit and storage. The plastic tray is generally rectangular and compartmented, and has openings or perforations through its bottom wall. The basin is substantially deeper than the tray which it receives and is dimensioned so that when the tray is oriented in one direction it may rest on the bottom of the basin, with the soak solution in the basin covering all of the instruments carried by the tray, and when oriented in a second position at right angles to the first it may be suspended by the basin with the tray's apertured bottom wall above the liquid level. Support shoulders are provided for suspending the tray in its second position, and stop means limit the extent of relative lateral movement of the tray in either of its positions. The basin includes means for restraining wave development and for reducing the possibilities of splashing and spilling should the basin be moved with liquid therein.

10 Claims, 8 Drawing Figures

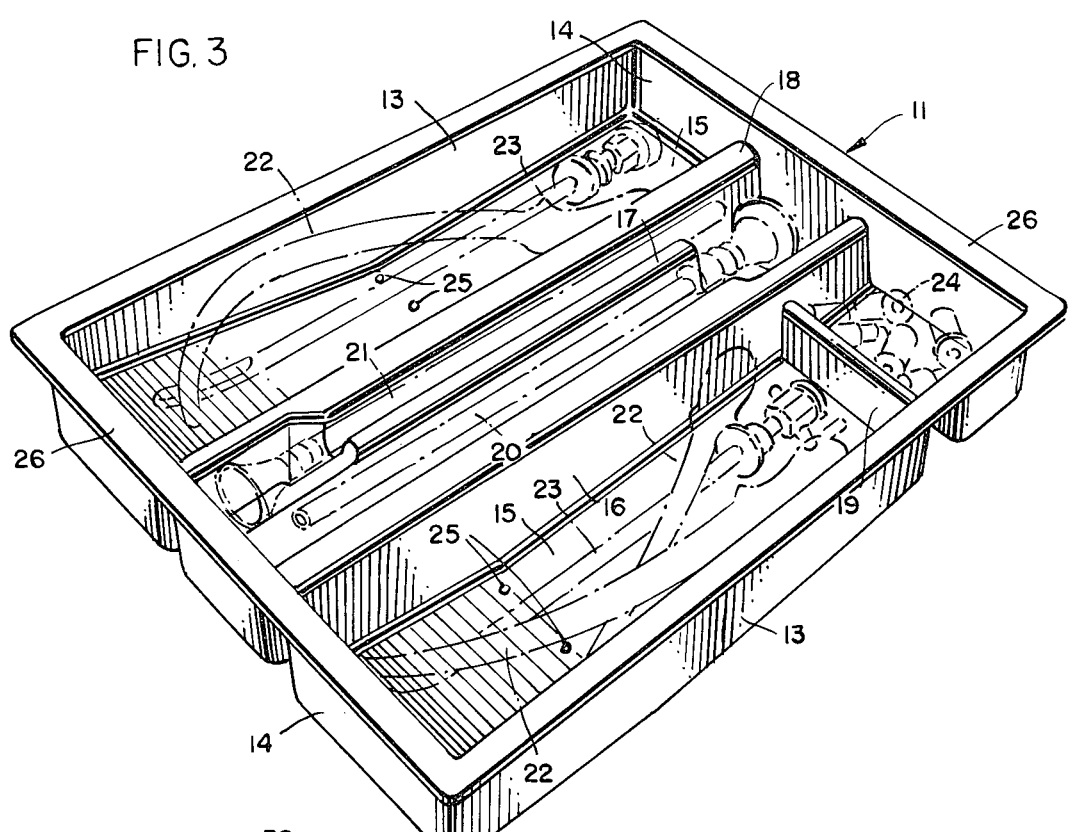
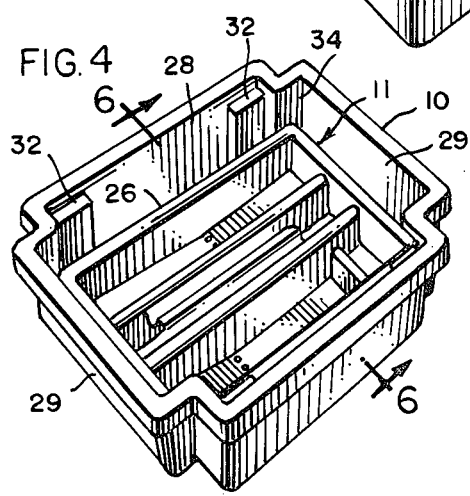
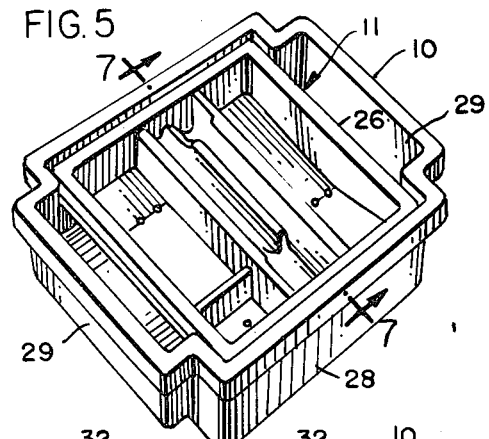
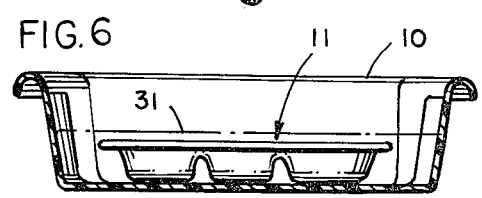
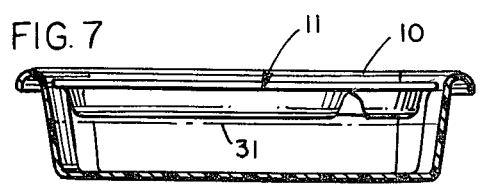
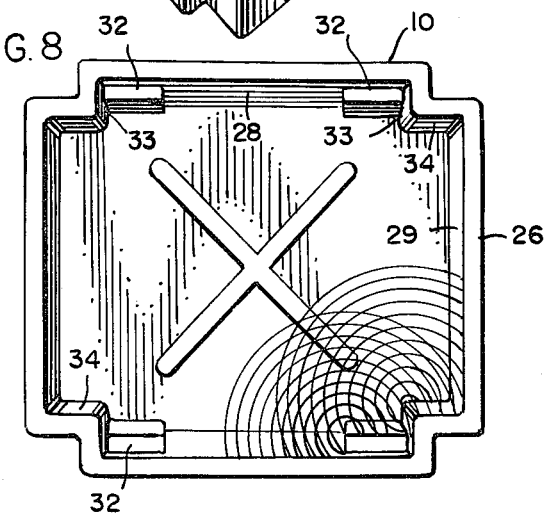

INSTRUMENT TRAY AND SOAK BASIN COMBINATION

BACKGROUND

Urological instruments are commonly disinfected by soaking them prior to use in a solution of buffered glutaraldehyde or some other strong disinfecting or sterilizing solution. While such a "cold soaking sterilization" procedure is most frequently associated with urological instruments, it may be used for disinfecting any instruments which are not capable of withstanding autoclaving temperatures or cannot conveniently be sterilized by other means.

Quite typically, all of the instruments required for a selected urological procedure are placed in a stainless steel basin containing the disinfecting or sterilizing solution and are simply soaked in that solution for a period of approximately 10 to 20 minutes. Thereafter, the instruments are grasped and lifted from the basin, rinsed, and laid out on a sterile-draped surface in the area of patient examination or operation.

A main disadvantage of the soaking and rinsing procedure as so described is that instrument damage has been found to occur with disturbing frequency. Some instruments or their parts are extremely delicate such as, for example, telescopes, fiber-optic light tubes, and cutting loops. By contrast, other instruments or parts commonly used in the same operative procedures are relatively sturdy and heavy. Since they are all treated in the soaking solution at the same time, and since they are ordinarily introduced into and removed from such a solution as a group, some damage to the more delicate (and expensive) components is not unusual.

Instrument damage through galvanic corrosion has also been a significant problem, especially because of the corrosive nature of the soak solutions and dissimilarities in the metallic composition of the instruments and the basins in which they are placed. Efforts to reduce such corrosion by lining the basins with towels have been only partially effective and, it is now suspected, may create a further problem by reducing the effectiveness of the solutions in disinfecting or sterilizing the instruments.

The recent use of plastic soaking basins has been more effective, although not completely so, in reducing instrument corrosion. Breakage and other instrument damage has continued to remain a problem notwithstanding the use of resilient plastic materials and even the use of perforated trays or baskets for introducing, supporting, and removing the instruments in mass in cold soaking procedures.

Patent references indicative of the state of the art are U.S. Pat. Nos. 3,807,954, 3,779,707, and 3,437,423.

SUMMARY

This invention is concerned with an instrument tray and basin which, through their construction and systematized usage, greatly reduces the likelihood of damage to the instruments during cold soaking sterilization procedures, rinsing procedures, storage, and transport from one station to the next. The improved tray and basin combination facilitates soaking and draining while reducing the risk that the corrosive soaking solution might splash or drip from the tray or basin onto other surfaces. In that regard, the basin is itself constructed to dissipate wave energy or break up wave development, thereby reducing the risk of splashing and spilling of liquid should movement of the basin be required.

Direct contact between the fragile instruments or parts and the heavier and less-delicate components during soaking, draining, and rinsing is prevented, or at least greatly reduced, by the construction of the tray and by the cooperative relationship between that tray and the basin. Also, isolation of the breakable components virtually eliminates the problem of corrosive damage to those parts.

In brief, the combination includes a generally rectangular instrument tray having upstanding side and end walls and having an apertured bottom wall. One or more upstanding partitions divide the interior of the tray into a plurality of instrument-receiving compartments, the height of the partitions and the upstanding walls being such that the instruments are received completely in the compartments without projecting therefrom. The soak basin has bottom, side and end walls defining an open-topped chamber for removably receiving the instrument tray, the chamber having a depth substantially greater than the height of the tray and being both longer and wider than the length of the tray (as measured from one upstanding end wall of the tray to the other). Thus, the tray is selectively receivable in the basin in either a first position, with the length of the tray extending longitudinally of the basin, or in a second position, with the length of the tray extending across the basin. Support shoulders are provided by the basin for engagement with the tray to support or suspend the tray with its perforated bottom wall above the bottom wall of the basin when the tray is in its second position. When so suspended, the bottom of the tray is spaced above the bottom wall of the basin a distance greater than the height of the tray itself. Consequently, the tray and its contents may be totally immersed in the treatment solution when the tray is in its first position, and may be suspended above the level of the liquid for draining when the tray is in its second position.

Other advantages and objects of the invention will become apparent from the drawings and detailed description.

DRAWINGS

FIG. 3 is an enlarged perspective view showing the tray with certain typical instruments disposed therein.

FIG. 4 is a perspective view showing the soak basin with an instrument tray disposed therein in a first position.

FIG. 5 is a perspective view similar to FIG. 4 but showing the instrument tray in a second position.

FIG. 6 is a sectional view of the basin taken along line 6—6 of FIG. 4, the tray being shown in elevation for clarity of illustration.

FIG. 7 is a sectional view of the basin taken along line 7—7 of FIG. 5, the tray being depicted in elevation for clarity of illustration.

FIG. 8 is a top plan view of the basin revealing the reentrant corner construction and its effect on wave propagation and development.

DETAILED DESCRIPTION

Figure 1:
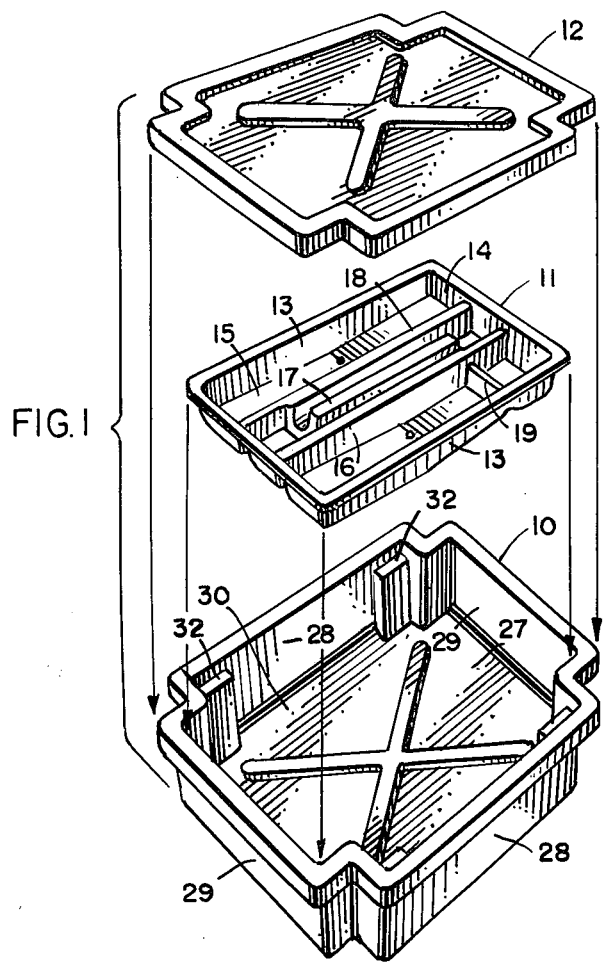
FIG. 1 is an exploded perspective view of a basin and tray embodying the invention, the combination being illustrated with an optional protective cover.

Referring to the drawings, the numeral 10 generally designates a soak basin adapted to receive an instrument tray 11. A cover 12 may be fitted upon the basin to reduce evaporation of treatment solution during periods of non-use and, in general, to protect against unnecessary exposure of the basin's contents. All three parts are preferably formed of plastic material. Polypropylene has been found particularly effective, but other durable and reatively rigid plastics may also be used.

Tray 11 is generally rectangular in configuration, having upstanding side and end walls 13 and 14, respectively, and having a bottom wall 15 formed integrally therewith. As shown most clearly in FIG. 3, the tray is divided by partitions 16–19 into a plurality of compartments for supporting various types of instruments. Of particular importance is the fact that the more delicate instruments, such as telescopes 20 and 21, are each supported in their own separate compartments, protected against possible contact with heavier and less-fragile instruments or components such as sheaths for resectoscopes and cystoscopes, urethral sounds and dilators, and the like. Typical sounds 22 and sheaths 23 are illustrated in the side compartments. A smaller compartment for stopcocks 24 and other small items may also be provided as shown.

At least one of the walls of the tray (e.g., bottom wall 15) is provided with perforations or openings 25 for the drainage of liquid from each of the compartments. Along the tops of side walls 13 and end walls 14 is a continuous integral outwardly-projecting flange or lip 26 which may be used for gripping the tray and, as described in detail hereafter, is an important element for suspending the tray within the basin. The height of upstanding walls 13 and 14, and of the partitions 16, 17, and 18, is such that the more delicate instruments 20 and 21 are protected against damaging contact with sounds and other elements that might be placed or even accidentally dropped into positions extending across the walls or partitions.

Like the instrument tray, basin 10 includes a bottom wall 27, side walls 28, and end walls 29. Such walls define an open-topped cavity or chamber 30 for receiving the instrument tray. The cavity is substantially deeper than the height of the tray and its length (between end walls 29) is greater tha the total length of the tray. Therefore, the tray may be lowered into the basin so that it rests upon the bottom wall thereof as illustrated most clearly in FIGS. 4 and 6. When so lowered, the tray 11 and its contents are totally immersed in the body of liquid within basin 10. The liquid level is represented in FIG. 6 by phantom line 31.

The width of chamber 30, as measured between side walls 28, is greater than the length of the tray as measured from the outer surfaces of upstanding end walls 14, with the result that the tray will nest within the chamber even when the tray extends in a transverse direction with respect to the basin (FIG. 5). Means are provided, however, for limiting the extent to which the reoriented tray may be lowered into the basin. In the illustration given, such means comprises support shoulders 32 which are formed integrally with the basin's side walls 28 and which project into the chamber at, or preferably slightly below (as shown), the upper limits of those side walls. Although the distance between shoulders 32 on opposite sides of the basin is greater than the length of the tray as measured from the outside surfaces of end walls 14, it is less than the total length of the tray measured from the edges of flanges 26. Consequently, when the tray is in its reoriented or second position, as illustrated in FIGS. 5 and 7, flanges 26 at the opposite ends of the tray engage shoulders 32 to suspend the tray with its bottom wall spaced a substantial distance above the bottom of the basin and above liquid level 31.

The shoulders 32, which constitute portions of side walls 28, may extend along the full length of the sides of the compartment instead of being formed as shown. As already suggested, they may also be flush with the tops of the side walls; however, the slightly lowered position of the shoulders is preferred because it permits drainage of liquid from flanges 26 with less chance of such liquid escaping from the basin, and because the optional cover 12 may seat more effectively upon the basin when the tray is in the instrument-draining position illustrated in FIGS. 5 and 7.

The corners of basin 10 have reverted or reentrant vertical surfaces which define stop means for limiting the extent of horizontal sliding movement of the tray in either its soaking position (FIG. 4) or its draining position (FIG. 5). Referring more specifically to FIG. 8, the generally vertical surfaces 33 are arranged in spaced opposing pairs, projecting inwardly from each side wall 28 of the basin. The opposing surfaces are spaced apart a distance slightly greater than the maximum width of the tray 11, with the result that such surfaces are engagable with the edges of flanges 26 of the tray to limit the extent of the tray's lateral movement when that tray is in its instrument-draining position (FIG. 5). It will also be noted that such stop means centers the tray to render the longitudinally-extending portions of flanges 26 more readily accessible for the purpose of lifting the tray from the basin.

The basin includes similar pairs of spaced upstanding surfaces 34 projecting inwardly from end walls 29. Again, each pair of surfaces 34 is spaced apart a distance slightly greater than the full width of the tray to limit the extent of movement of the tray relative to the basin when the parts are nested together in the manner illustrated in FIGS. 4 and 6. Since the surfaces 34 also serve to center the tray within the basin, the longitudinal flange portions of the tray are spaced from the basin's side walls 28 and are readily accessible for the purpose of lifting the tray from its fully lowered position.

Besides providing surfaces for guiding and centering the tray within the basin, the reentrant corners has been found to reduce splashing and spilling of liquid from the basin when the basin is moved from one location to another. The reason is illustrated somewhat schematically in FIG. 8. The development of a wave from any side wall of the basin is impeded by interference from waves which emanate from the corners, resulting in an interference which tends to reduce wave size or amplitude.

Figure 2:
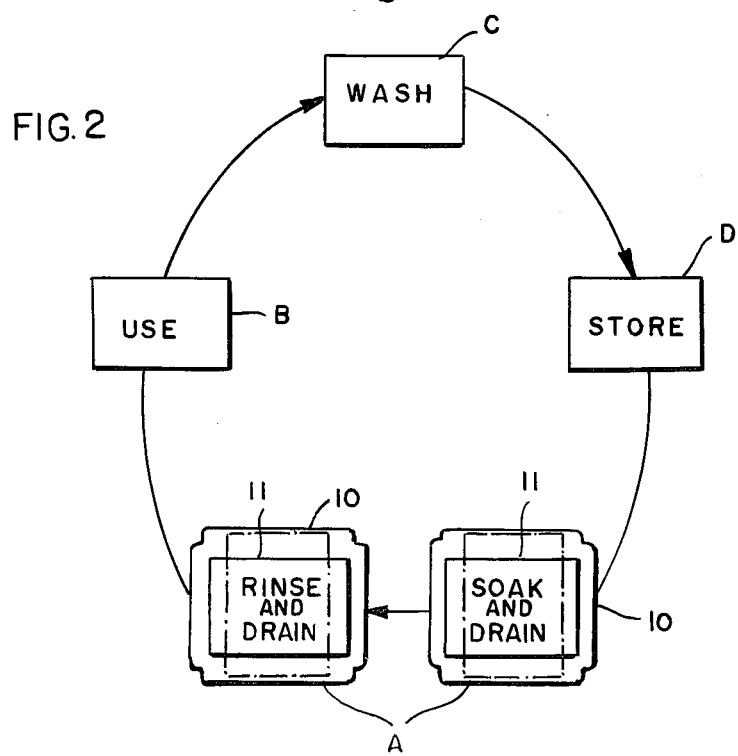
FIG. 2 is a diagram illustrating the pattern of usage of the instrument tray and soak basin.

FIG. 2 schematically depicts a recommended procedure for using the tray-basin combination. A pair of basins 10 are located at station A, one basin containing a suitable sterilizing or disinfecting agent, such as an aqueous solution of glutaraldehyde, and the other containing sterile water. An instrument tray 11, containing a set of instruments required for a given operating procedure, is lowered fully into the basin containing the treatment agent. After a predetermined interval, ordinarily about 20 minutes, the tray 11 is shifted in the same basin into its instrument-draining position, thereby permitting treatment agent to drain back into the basin from the tray. Thereafter, the tray is shifted into fully lowered position into the neighboring basin containing sterile water and, after the instruments have been fully rinsed, the tray is again repositioned in an instrument-draining position (depicted in phantom lines).

The drained instruments are then ready for use and are carried by means of the tray to the operative area, station B. Following use, they are washed and replaced in the tray at station C. The washed and dried instruments, positioned in appropriate compartments of the tray, are then placed in storage (station D) until they are again needed in an operative procedure requiring such an instrument set. It is to be noted that from the time such instruments are washed and placed into their compartments, and throughout the period of storage, the soaking and draining procedure, the rinsing and draining procedure, and until they are removed at station B for use in an operative procedure, the instruments remain in the same compartments of the same tray. Since the more delicate instruments, such as the telescopes, are segregated in their own compartments, they remain protected by the tray throughout storage, during the soaking, draining and rinsing procedures, and during transport from washing until use.

While in the foregoing an embodiment of the invention has been disclosed in considerable detail for purposes of illustration, it will be understood by those skilled in the art that many of these details may be varied without departing from the spirit and scope of the invention.

I claim:

1. In combination, a generally rectangular instrument tray having a bottom wall and having side and end walls upstanding from said bottom wall, at least one of said walls having apertures so positioned therein to provide for the substantially complete drainage of fluid from said tray; said tray having a length, measured from one upstanding end wall to the other, substantially greater than its width, measured from one upstanding side wall to the other; and a soak basin having bottom, side, and end walls defining a chamber for removably receiving said tray; said chamber having a depth substantially greater than the height of the upstanding walls of said tray and being both longer and wider than said length of said tray; whereby, said tray is selectively receivable in said chamber in a first position wherein the length of said tray extends longitudinally of said basin and in a second position wherein said length of said tray extends transversely of said basin; support means provided by said basin for supporting said tray in a fluid drainage and instrument storage position with its bottom wall spaced a substantial distance above the basin's bottom wall when said tray is in its second position; stop means provided by said basin and engagable with said tray for preventing relative horizontal movement of said tray without restraining relative vertical upward movement of the tray when said tray is in its second position; and flanges projecting outwardly from the top of said end walls of said tray; said support means comprising shoulders provided by said side walls of said basin; said shoulders being engagable with said flanges for supporting said tray in its elevated second position.

2. The combination of claim 1 in which said side walls of said tray are provided with outwardly projecting flanges merging with the flanges of said end walls of said tray.

3. The combination of claim 1 in which said shoulders project inwardly into said chamber from said side walls of said basin.

4. The combination of claim 3 in which said shoulders are spaced below the upper limits of the basin's side walls.

5. The combination of claim 3 in which a pair of said shoulders are provided along each of said side walls of said basin; said shoulders of said pair being located adjacent opposite ends of each side wall of said basin.

6. In combination, a generally rectangular instrument tray having a bottom wall and having side and end walls upstanding from said bottom wall, at least one of said walls having apertures so positioned therein to provide for the substantially complete drainage of fluid from said tray; said tray having a length, measured from one upstanding end wall to the other, substantially greater than its width, measured from one upstanding side wall to the other; and a soak basin having bottom, side, and end walls defining a chamber for removably receiving said tray; said chamber having a depth substantially greater than the height of the upstanding walls of said tray and being both longer and wider than said length of said tray; whereby, said tray is selectively receivable in said chamber in a first position wherein the length of said tray extends longitudinally of said basin and in a second position wherein said length of said tray extends transversely of said basin; support means provided by said basin for supporting said tray in a fluid drainage and instrument storage position with its bottom wall spaced a substantial distance above the basin's bottom wall when said tray is in its second position; and stop means provided by said basin and engageable with said tray for preventing relative horizontal movement of said tray without restraining relative vertical upward movement of the tray when said tray is in its second position; said stop means comprising pairs of spaced upstanding opposing surfaces provided along each side wall of said basin; said opposing surfaces being spaced apart a distance slightly greater than the width of said tray at each end thereof for limiting horizontal movement of said tray upon engagement with the side walls of said tray.

7. The combination of claim 6 in which said support means is engageable with said tray to support the tray with its bottom wall spaced above the basin's bottom wall at a distance greater than the height of the tray's upstanding walls.

8. The combination of claim 6 in which said pairs of spaced upstanding opposing surfaces project inwardly from each side wall of said basin.

9. The combination of claim 8 in which said basin is also provided with second stop means for limiting the extent of lateral sliding movement of said tray when the same is in its first position, said second stop means including pairs of spaced upstanding opposing second surfaces projecting inwardly from each end wall of said basin; said pairs of second surfaces being spaced apart a distance slightly greater than the width of said tray at each end thereof for limiting the extent of lateral movement of said tray when the same is in its first position.

10. The combination of claim 9 in which said second surfaces merge with said first-mentioned surfaces to define reentrant corner portions of said basin; said reentrant corner portions producing wave interference for reducing possibilities of splashing and spilling when said basin is moved with liquid contained therein.

* * * * *